United States Patent [19]
Widlund

[11] Patent Number: 5,919,178
[45] Date of Patent: Jul. 6, 1999

[54] METHOD FOR PRODUCING AN ABSORBENT STRUCTURE WHICH INCLUDES A LAYER OF SUPERABSORBENT MATERIAL

[75] Inventor: Urban Widlund, Mölnlycke, Sweden

[73] Assignee: SCA Mölnlycke AB, Gothenburg, Sweden

[21] Appl. No.: 08/718,571

[22] PCT Filed: Apr. 10, 1995

[86] PCT No.: PCT/SE95/00383

§ 371 Date: Oct. 2, 1996

§ 102(e) Date: Oct. 2, 1996

[87] PCT Pub. No.: WO95/30396

PCT Pub. Date: Nov. 16, 1995

[30] Foreign Application Priority Data

May 4, 1994 [SE] Sweden ................................. 9401541

[51] Int. Cl.⁶ .............................. A61F 13/15; A61F 13/20
[52] U.S. Cl. .......................... 604/368; 604/367; 604/379; 156/276; 156/308.8
[58] Field of Search ..................................... 604/365, 367, 604/368, 378, 379; 156/62.2, 62.8, 324.4, 308.8, 276; 428/228; 442/118

[56] References Cited

U.S. PATENT DOCUMENTS

| | | | |
|---|---|---|---|
| 3,017,304 | 1/1962 | Burgeni . | |
| 4,057,061 | 11/1977 | Ishikawa et al. | 128/284 |
| 4,134,948 | 1/1979 | Baker, Jr. | 264/518 |
| 4,186,165 | 1/1980 | Aberson et al. . | |
| 4,217,901 | 8/1980 | Bradstreet et al. | 128/290 |
| 4,260,443 | 4/1981 | Lindsay et al. | 156/220 |
| 4,537,590 | 8/1985 | Pieniak et al. . | |
| 4,600,458 | 7/1986 | Kramer et al. | 156/276 |
| 4,851,069 | 7/1989 | Packard et al. | 156/276 |
| 5,300,192 | 4/1994 | Hansen et al. | 162/184 |
| 5,525,407 | 6/1996 | Yang | 428/218 |
| 5,693,162 | 12/1997 | Gustafsson et al. | 156/62.2 |

FOREIGN PATENT DOCUMENTS 153066   6/1988   Denmark .

*Primary Examiner*—Mickey Yu
*Assistant Examiner*—Tram A. Nguyen
*Attorney, Agent, or Firm*—Young & Thompson

[57] ABSTRACT

A method for producing an absorbent structure intended for use in an absorbent article, such as a sanitary napkin, incontinence guard, diaper, wherein the absorbent structure is produced by laying a layer of essentially superabsorbent material between two layers of defibered and moisturized cellulose pulp or tissue, whereafter the composite structure is calendared between one or more pairs of heated rolls, wherewith the layer of superabsorbent material binds in itself and forms a stable layer, which binds to the surrounding cellulose pulp layers or tissue layers. The absorbent structure exhibits excellent absorption properties and can be made very thin. The structure can be manufactured without superabsorbent material being spread around the manufacturing machine during the production process, or escaping from the finished absorbent article when packaging, transporting or using the article.

25 Claims, 1 Drawing Sheet

METHOD FOR PRODUCING AN ABSORBENT STRUCTURE WHICH INCLUDES A LAYER OF SUPERABSORBENT MATERIAL

BACKGROUND

The present invention relates to a method for producing an absorbent structure for use in an absorbent article, such as a sanitary napkin, incontinence guard, diaper and like articles.

Many different types of absorbent articles of this kind are known to the art. The absorbent body of such articles is produced conventionally by dry-defibering cellulose pulp contained, for instance, in reels, bales or sheets, and converting the cellulose pulp in a fluff state to a pulp mat, sometimes while mixing so-called superabsorbents in the pulp mat, these superabsorbents being polymers which are capable of absorbing many times their own weight in liquid or body fluid.

EP 0,122,042 describes a method of manufacturing an absorbent structure which includes superabsorbent material. The cellulose pulp is first defibered to form cellulose fibres, so-called fluff pulp, whereafter a mixture of these fibres and water-insoluble hydrogel particles are air-laid to form a web from which the absorbent structure is formed and subsequently compressed to a density of 0.15–1.0 g/cm$^3$.

The pulp body is compressed with the intention of reducing its bulk and also with the intention of enhancing its liquid wicking properties. With the majority of sanitary products a thin article is desired so that the article can be worn as discretely as possible.

Superabsorbent material is normally used in the form of granules or small particles. It may be found difficult to bind these small particles satisfactorily in the absorbent structure, which is one problem associated with the use of superabsorbent material. The method described, for instance, in EP 0,122,042 involves the risk of superabsorbent material being spread in and around the manufacturing plant, and also involves the risk of particles of superabsorbent material escaping from the finished pulp core when packaging, transporting or using the core. When manufacturing products which include superabsorbent material, the aforesaid problems become greater with thinner products.

Superabsorbent particles often have sharp edges and are therefore at times able to perforate the liquid-impermeable sheets of absorbent articles, unless preventative measures are taken. It is also important to obtain intimate contact between fibres and superabsorbent material, in order to achieve effective transference of liquid between the two materials.

Furthermore, the absorbent body may include other ingredients that are intended, for instance, to improve its ability to take-up or disperse liquid, or to increase its coherency and its ability to resist deformation while in use.

A very large part of the production plant used by the manufacturers of the aforesaid sanitary articles is comprised of defibrating equipment, pneumatic conveyor systems and mat-forming equipment. This production plant is often followed by equipment for compressing the finished pulp mat or the finished sanitary product.

It is known from U.S. Pat. No. 3,017,304 that a surface sheet containing paper bonds and having a higher density and greater strength than the original cellulose pulp mat can be obtained, by spraying water onto a cellulose pulp mat and then compressing the mat. Such a layer is sometimes called a "Burgeni layer". It is also known from U.S. Pat. No. 4,186,165 to compress a cellulose pulp mat that contains superabsorbent material with the aid of heated rolls and without adding water, and therewith obtain in the cellulose pulp mat an inner layer which has a higher density and greater strength than in the original pulp mat. The particles of superabsorbent material are bound to the structure in this layer, and the layer can also be obtained at a desired level in the structure by varying the temperature difference between the rolls. However, when practicing this method, the particles of superabsorbent material that are present in remaining parts of the pulp mat remain only loosely bound in the structure. Neither is it possible with this method to obtain a structure in which only one layer contains superabsorbent material and where this layer is surrounded by one or more layers which are free from such material, which is desired in some product applications.

SUMMARY OF THE INVENTION

An object of the present invention is to provide a thin absorbent structure which includes a layer which contains bound superabsorbent material and which can be included in an absorbent article of the kind defined in the introduction. The absorbent structure shall exhibit very good absorption properties and it shall be possible to produce the structure without spreading superabsorbent material around the manufacturing plant during the production process, or without the superabsorbent material escaping from the finished absorbent article when packaging, transporting or using the article.

This object is achieved by means of the present invention, in that the absorbent structure is produced by placing a layer that contains essentially superabsorbent material between two layers of defibered and moistened cellulose pulp or tissue, and then calendaring the composite structure between one or more heated pairs of rolls, wherein the moisture in the immediate proximity of the heated rolls is vapourized by the heat emitted therefrom and then condensed in the colder layer of superabsorbent material located further down in the material, and wherein said layer is self-binding and able to form a stable layer; and in that said layer is bound to the surrounding cellulose pulp layers or tissue layers.

DESCRIPTION OF THE INVENTION

Figure 1:
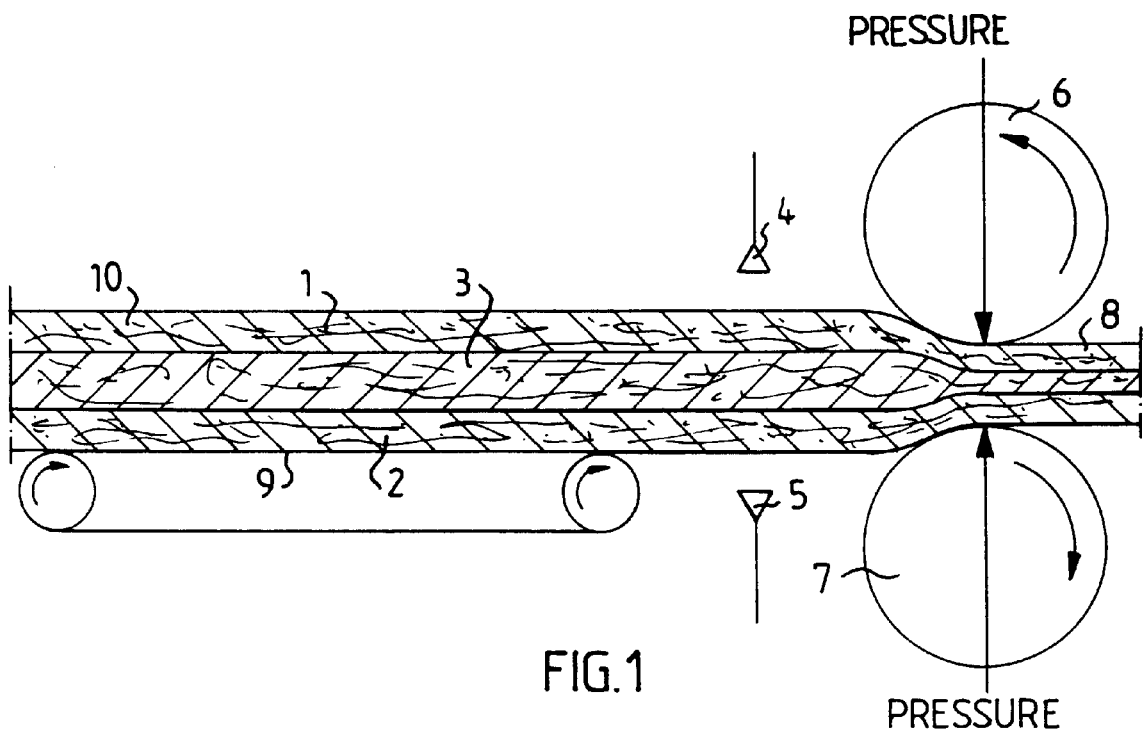
FIG. 1 illustrates schematically equipment for manufacturing an absorbent structure in accordance with the inventive method.

The object of the present invention is to provide an absorbent structure which includes superabsorbent material and which can be included in an absorbent article, such as a sanitary napkin, panty guard, incontinence guard, diaper and like articles. The liquids concerned are primarily urine and blood. The absorbent structure shall exhibit very good absorption properties, both with regard to its ability to quickly take-up liquid and its ability to disperse the liquid throughout the material. Certain layers of the absorbent structure will preferably contain no superabsorbent material, and it shall be possible to produce a very thin structure. It shall also be possible to produce the structure without spreading superabsorbent material in and around the manufacturing machine during the manufacturing process and without articles of superabsorbent material escaping from the finished pulp core or from the absorbent article when packaging, transporting or using the article.

This object has been achieved in accordance with the invention by producing the absorbent structure in accordance with a method in which a layer that contains essentially superabsorbent material is placed between two layers of defibered and moistened cellulose pulp or moistened tissue, and then calendaring the composite structure by compressing the structure between one or more heated pairs of rolls. The moisture in the immediate proximity of the heated rolls is vapourized by the heat emitted therefrom and is then condensed in the colder layer of superabsorbent material located deeper in the material. This layer is herewith bound in its self and formed into a stable layer, and the layer is bound to the surrounding cellulose pulp layers or tissue layers. The cellulose pulp or the tissue used may be moist from the outset or may be moistened at an early stage of the manufacturing process, although the outer surfaces of the cellulose pulp or the tissue may advantageously be sprayed with moisture immediately prior to calendaring the pulp, which simplifies the manufacturing process while still enabling moisture to be transported in- to the layer of superabsorbent material in the compression and heating stage. When an upper or lower layer is constituted of cellulose pulp, the moisture content of this layer shall be 10–40%, preferably 15–30% and more preferably 20–25%, calculated on the dry weight of the cellulose pulp. When an upper or lower layer is constituted of tissue, the moisture content of this layer shall be 20–70%, preferably 40–60% and more preferably 45–55%, calculated on the dry weight of the tissue layer.

The properties of the different layers in the structure can be controlled to suit different product applications, by using as the starting materials for the absorbent structure, two separate fluff pulp layers or tissue layers between which the layer of superabsorbent material is placed. One or both of the fluff pulp layers may, for instance, be free from superabsorbent material. The various fluff pulp layers may be comprised of different cellulose pulps or may be the same type of cellulose pulp, for instance fibres of chemithermomechanically produced pulp (CTMP) having a curl value of 0.20–0.40, or a corresponding product produced from sulphite or sulphate pulp, so-called chemical cellulose pulp. Cellulose fibres that have been stiffened chemically or in some other way may also be used in one or in both layers. When fibres of chemithermomechanically produced pulp are used, these fibres may be flash-dried fibres for instance.

DESCRIPTION OF EXEMPLIFYING EMBODIMENTS

FIG. 1 schematically illustrates equipment for manufacturing an absorbent structure in accordance with the invention. There is formed on a wire 9 a web 10 that has a surface weight of 100–1,000 gm/m$^2$ and a density of 0.05–0.2 g/cm$^3$. The web comprises an upper layer in the form of an upper pulp web 1 having a surface weight of 100–1,000 g/m$^2$ and a density of 0.05–0.2 g/cm$^3$, and a lower pulp web 2 having a surface weight of 50–1,000 g/m$^2$ and a density of 0.05–0.2 g/cm$^3$, and a layer of essentially superabsorbent material 3 lying between said upper and lower layers and having a surface weight of 50–500 g/m$^2$ and a density of 0.4–0.7 g/cm$^3$. Water is sprayed onto the web 10 with the aid of spray nozzles 4 and 5, to obtain a moisture content of 15–40 percent, calculated on the total weight of the web in a dry state. The web 10 is compressed to a density of 0.1–0.5 g/cm with the aid of the heated rolls 6 and 7, causing the superabsorbent layer 3 to bind to the two layers 1 and 2. The rolls 6 and 7 have a line pressure of 100–200 kg/cm and a temperature of 120–250° C. The compressed pulp mat 8 has a thickness of 1–4 mm.

Figure 2:
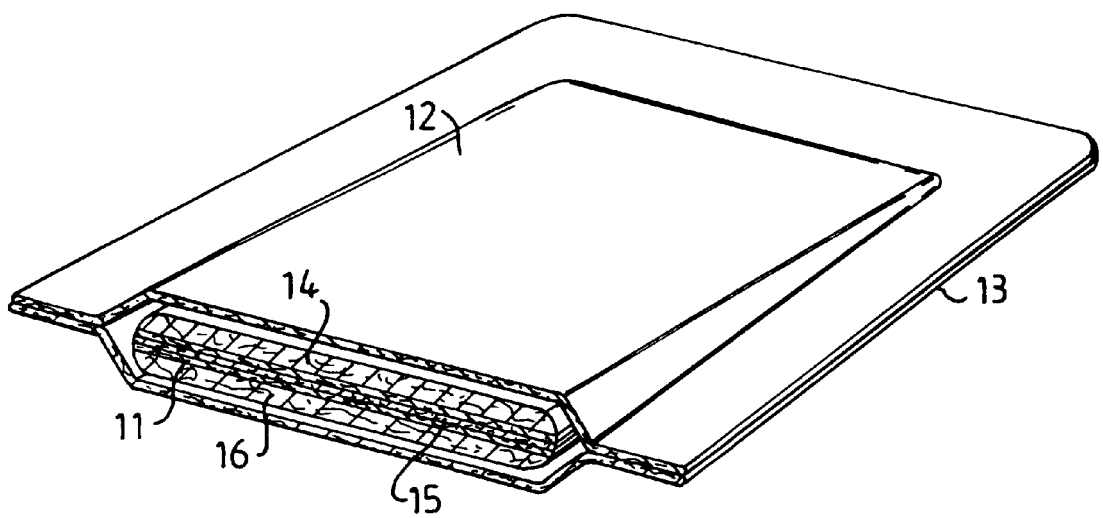
FIG. 2 illustrates schematically an exemplifying embodiment of an absorbent article produced in accordance with the invention.

FIG. 2 illustrates a diaper manufactured by the method according to one embodiment of the invention. The diaper typically comprises an absorbent body 11 enclosed between a liquid-permeable top sheet 12, which is suitably comprised of a soft nonwoven material, a perforated plastic film or the like, and which lies proximal to the wearer in use, and a liquid-impermeable bottom or backing sheet 13. The sheets 12 and 13 have parts which extend beyond the absorbent body 11 and are joined together at these parts. The bottom sheet 13 is comprised of a suitable plastic material, for instance polyethylene. It will be understood that the top and the bottom sheets may be comprised of other known materials, within the scope of the invention. The absorbent body 11 may be manufactured totally of the inventive material, or with a combination of inventive material and other material.

If the absorbent structure is manufactured totally from an inventive material, it may have the following construction comprising the various layers of different properties obtained in accordance with the invention. The absorbent structure will then have an upper liquid or fluid entry layer 14, an intermediate layer 15 and a bottom layer 16.

The purpose of the entry layer 14 is to take-up and disperse a given quantity of liquid quickly. The liquid shall be held loosely in the fibre structure and drained rapidly therefrom. The entry layer 14 is preferably comprised of an upper layer of inventive material and is composed of relatively stiff or rigid fibres which provide a relatively open fibre structure, even after compression and wetting. For instance, the entry layer 14 may be comprised of chemically stiffened cellulose fibres and will preferably contain less than 10 percent superabsorbent material, calculated on the weight of the structure in a dry state.

The purpose of the intermediate layer 15 is to bind absorbed liquid in the interior of the absorbent structure, so as to prevent liquid returning and wetting the wearer's skin. The intermediate layer 15 contains a high percentage of superabsorbent material, a suitable percentage in this respect being 60–90 percent by weight calculated on the weight of the structure in a dry state.

The purpose of the bottom layer 16 is to disperse the liquid that penetrates through the intermediate layer 15 to parts of the absorbent body 1 that have not yet been utilized. Another purpose of the bottom layer 16 is to protect the liquid-impermeable bottom sheet 13 against perforation by particles of superabsorbent material. The bottom layer 16 is preferably comprised of the bottom layer of a material that has been constructed in accordance with the invention, and may be comprised of chemical fluff pulp and contain 5–20 percent superabsorbent material calculated on the weight of the structure in a dry state.

The various layers may have different shapes and sizes. The absorbent structure is normally combined with some type of elastication, among other things in the crotch region, so as to improve the fit and the function of the product.

It will be understood that the invention is not restricted to the illustrated exemplifying embodiment thereof and that other embodiments are conceivable within the scope of the following claims.

I claim:

1. A method for producing an absorbent structure in an absorbent article selected from the group consisting of a diaper, a sanitary napkin, a panty guard, and an incontinence guard, which comprises:

laying an intermediate layer containing essentially superabsorbent material between an upper absorbing layer and a bottom absorbing layer of defibered cellulose pulp moisturized to at least 10%, or tissue moisturized to at least 20%, calculated on the weight of the cellulose pulp or the tissue in a dry state, to obtain a composite structure, said intermediate layer containing at least 60% by weight of superabsorbent material calculated on the weight of the cellulose or the tissue in a dry state;

thereafter compressing the composite structure between one or more heated pairs of rolls whereby the moisture in the immediate proximity of the heated rolls is vaporized by the heat and condensed in the intermediate layer of superabsorbent material, and wherein the intermediate layer is self-binding and able to form a stable layer, and also binds to the surrounding cellulose pulp layers or tissue layers.

2. The method according to claim 1, wherein at least one upper or one bottom layer is constituted of defibered cellulose pulp which is moisturized to a moisture content of 10–40%, calculated on the weight of cellulose pulp or the tissue in a dry state.

3. The method according to claim 2, wherein the defibered cellulose pulp is moisturized to a moisture content of 20–25%, calculated on the weight of the cellulose pulp or the tissue in a dry state.

4. The method according to claim 1, wherein at least one upper or one bottom layer is constituted of tissue, which is moisturized to a moisture content of 20–70%, calculated on the weight of the cellulose pulp or the tissue in a dry state.

5. The method according to claim 4, wherein the tissue is moisturized to a moisture content of 45–55%, calculated on the weight of the cellulose pulp or the tissue in a dry state.

6. The method according to claim 1, wherein the intermediate layer originally contains at least 90% of superabsorbent material, calculated on the weight of the cellulose pulp or the tissue in a dry state.

7. An absorbent structure for use in an absorbent article selected from the group consisting of a diaper, a sanitary napkin, a panty guard, and an incontinence guard, the absorbent structure comprising:

a composite structure including
an upper absorbing layer;
a bottom absorbing layer;
the upper absorbing layer and bottom absorbing layer being comprised of defibered cellulose pulp moisturized to at least 10%, or tissue moisturized to at least 20%, calculated on the weight of the cellulose pulp or the tissue in a dry state;
an intermediate layer comprised of at least 60% by weight of superabsorbent material, calculated on the total weight of the composite structure in a dry state, positioned between the upper absorbing layer and the bottom absorbing layer;
the composite structure having been compressed between at least one pair of heated rolls so as to vaporize the moisture in the immediate proximity of the heated rolls and condense such moisture in the intermediate layer;
wherein the intermediate layer is self-binding and able to form a stable layer, and also binds to the surrounding cellulose pulp layers or tissue layers.

8. The absorbent structure according to claim 7, wherein the density of the intermediate layer which contains superabsorbent material ranges from 0.2 to 1.0 g/cm$^3$.

9. The absorbent structure according to claim 7, wherein the density of the intermediate layer ranges from 0.3 to 0.7 g/cm$^3$.

10. The absorbent structure according to claim 7, wherein the uppermost absorbing layer has a density ranging from 0.05 to 0.4 g/cm$^3$.

11. The absorbent structure according to claim 10, wherein the uppermost absorbing layer has a density ranging from 0.15 to 0.25 g/cm$^3$.

12. The absorbent structure according to claim 7, wherein the bottom absorbing layer has a density ranging between 0.1 to 0.5 g/cm$^3$.

13. The absorbent structure according to claim 12, wherein the bottom absorbing layer has a density ranging between 0.2 to 0.3 g/cm$^3$.

14. The absorbent structure according to claim 7, wherein the surface weight ranges from 50 to 1,500 g/m$^2$.

15. The absorbent structure according to claim 14, wherein the surface weight ranges from 200 to 600 g/m$^2$.

16. The absorbent structure according to claim 7, wherein the cellulose fibers in at least one of the upper absorbing layer and the bottom absorbing layer are comprised essentially of fibers of chemithermomechanically produced pulp.

17. The absorbent structure according to claim 16, wherein the chemithermomechanical pulp fibers have a curl value of 0.20–0.40.

18. The absorbent structure according to claim 16, wherein the cellulose fibers are comprised essentially of flash-dried cellulose fibers.

19. The absorbent structure according to claim 7, wherein the cellulose fibers in at least one of the upper absorbing layer and the bottom absorbing layer are comprised essentially of fibers of chemically produced pulp.

20. The absorbent structure according to claim 7, wherein at least some of the fibers are stiffened cellulose fibers.

21. The absorbent structure according to claim 7, wherein the percentage of superabsorbent material in the upper absorbing layer is lower than 10% by weight, calculated on the total weight of the composite structure in a dry state.

22. The absorbent structure according to claim 7, wherein the percentage of superabsorbent material in the bottom absorbing layer is at most 20% by weight, calculated on the total weight of the composite structure in a dry state.

23. The absorbent structure according to claim 22, wherein the percentage of superabsorbent material in the bottom absorbing layer is at most 10% by weight, calculated on the total weight of the composite structure in a dry state.

24. The absorbent structure according to claim 7, wherein the finished absorbent structure has a moisture content of 3–20% by weight, calculated on the total weight of the absorbent structure.

25. An absorbent article selected from the group consisting of a diaper, a sanitary napkin, a panty guard, and an incontinence guard, the article comprising: a liquid-permeable top sheet, a generally liquid-impermeable bottom sheet, and an absorbent body placed therebetween, wherein the absorbent body includes the absorbent structure according to claim 7.

* * * * *